(12) United States Patent
Ruff

(10) Patent No.: US 9,398,878 B2
(45) Date of Patent: Jul. 26, 2016

(54) SKIN TENSIOMETER

(71) Applicant: Gregory L. Ruff, Chapel Hill, NC (US)

(72) Inventor: Gregory L. Ruff, Chapel Hill, NC (US)

( * ) Notice: Subject to any disclaimer, the term of this patent is extended or adjusted under 35 U.S.C. 154(b) by 4 days.

(21) Appl. No.: 14/215,551

(22) Filed: Mar. 17, 2014

(65) Prior Publication Data

US 2014/0276232 A1 Sep. 18, 2014

Related U.S. Application Data

(60) Provisional application No. 61/792,784, filed on Mar. 15, 2013.

(51) Int. Cl.
*A61B 5/00* (2006.01)

(52) U.S. Cl.
CPC ............... *A61B 5/442* (2013.01); *A61B 5/4872* (2013.01)

(58) Field of Classification Search
CPC .. A61B 5/0053; A61B 5/4872; A61B 5/1075; A61B 5/442
See application file for complete search history.

(56) References Cited

U.S. PATENT DOCUMENTS

| | | | |
|---|---|---|---|
| 1,879,941 A | 9/1932 | McCabe | |
| 3,008,239 A | 11/1961 | Lange | |
| 3,140,546 A | 7/1964 | Bartlett | |
| 4,127,112 A | 11/1978 | Sherlock et al. | |
| 4,233,743 A | 11/1980 | Flick | |
| 4,312,363 A | 1/1982 | Rothfuss et al. | |
| 4,315,372 A | 2/1982 | Kinkead | |
| 5,156,161 A | 10/1992 | Lollar | |
| 8,394,020 B2* | 3/2013 | Duncan | A61B 5/0053 600/300 |

OTHER PUBLICATIONS

Carlyon, R. G., et al., Apparatus for precision calibration of skinfold calipers, American Journal of Human Biology, 1998, pp. 689-697, vol. 10, issue 6.
Lafayette Instrument, Skinfold Caliper II Body Fat Caliper, Feb. 27, 2014, http://prohealthcareproducts.com/body-fat-measurement-c-8/lafayette-skinfold-caliper.
Topend Sports Network, Skinfold Caliper Guide, Feb. 27, 2014, http://www.topendsports.com/testing/skinfold-caliper-guide.htm.
Accu-Measure Fitness 3000 Personal Body Fat Tester, Feb. 27, 2014, http://www.amazon.com/Accu-Measure-Fitness-3000-Personal-Tester/dp/B000G7YW74/.

* cited by examiner

*Primary Examiner* — Max Hindenburg
(74) *Attorney, Agent, or Firm* — Michael G. Johnston; Moore & Van Allen PLLC

(57) ABSTRACT

An apparatus for measuring tension of skin comprises a first rigid leg, a second rigid leg, and means for pivotally connecting proximal ends of the first leg and the second leg such that distal ends of the first leg and the second leg can be moved toward and away from one another. A gauge is carried by one of the first leg or the second leg for giving an indication of the spacing between the distal ends of the first leg and the second leg. Indicia is carried by the other of the first leg or the second leg. A spring arm is connected for resilient, flexible movement relative to one of the first leg or the second leg.

8 Claims, 3 Drawing Sheets

SKIN TENSIOMETER

CROSS REFERENCES

This application is related to U.S. provisional application No. 61/792,784, filed Mar. 15, 2013, entitled "SKIN TENSIOMETER", naming Gregory L. Ruff as the inventor. The contents of the provisional application are incorporated herein by reference in their entirety, and the benefit of the filing date of the provisional application is hereby claimed for all purposes that are legally served by such claim for the benefit of the filing date.

BACKGROUND

A skin tensiometer is described for measuring the tension in a portion of skin at a body site and, more particularly, a skin tensiometer which may inform a doctor of skin tension during a surgical procedure such as a facelift.

It is necessary during some surgical procedures to determine the tension of a portion of the skin. This is particularly true during a facelift procedure wherein the tension or tautness in a portion of the skin is enhanced as a part of the procedure. Typically, a surgeon will simply using her fingers to evaluate skin tension. The goal is to avoid either too tight of skin that can strain against ligatures, causing edema and scarring or, too loose of skin that diminishes the aesthetic outcome desired.

A skinfold skin tension measuring apparatus is used for self-measurement of the thickness of a subcutaneous layer of fat to obtain the body fat percentage of a person. The skinfold skin tension measuring apparatus has a pair of rigid arms pivotally connected at one end with opposed clamping surfaces at the other end. The rigid arms can be pivoted for moving the clamping surfaces between open and closed positions. The skin tension measuring apparatus is used by grasping a skinfold with the opposed clamping surfaces by compressing the arms toward one the closed position. The skin fold skin tension measuring apparatus pull the subcutaneous layer of fat away from the underlying muscle tissue at the measurement site. A gauge or scale may be provided in order to obtain a reading as to the distance separating the clamping surfaces. The gauge may take the form of an arcuate bar carried by one of the legs of the skin tension measuring apparatus. Unfortunately, the conventional skinfold skin tension measuring apparatus cannot be used to determine skin tension.

For the foregoing reasons, there is a need for an apparatus for measuring the tension in a portion of skin at a body site.

SUMMARY

An apparatus for measuring tension of skin is provided. The skin tension measuring apparatus comprises a first rigid leg, a second rigid leg, and means for pivotally connecting proximal ends of the first leg and the second leg such that distal ends of the first leg and the second leg can be moved toward and away from one another. A gauge is carried by one of the first leg or the second leg for giving an indication of the spacing between the distal ends of the first leg and the second leg. Indicia is carried by the other of the first leg or the second leg. A spring arm is connected for resilient, flexible movement relative to one of the first leg or the second leg.

BRIEF DESCRIPTION OF THE DRAWINGS

For a more complete understanding of the present invention, reference should now be had to the embodiments shown in the accompanying drawings and described below. In the drawings.

DESCRIPTION

Certain terminology use is used herein for convenience only and is not to be taken as a limitation on the invention. For example, words such as "upper," "lower," "left," "right," "horizontal," "vertical," "upward" and "downward" merely describe the configuration shown in the figs. Indeed, the components may be oriented in any direction and the terminology, therefore, should be understood as encompassing such variations unless specified otherwise.

Figure 1:
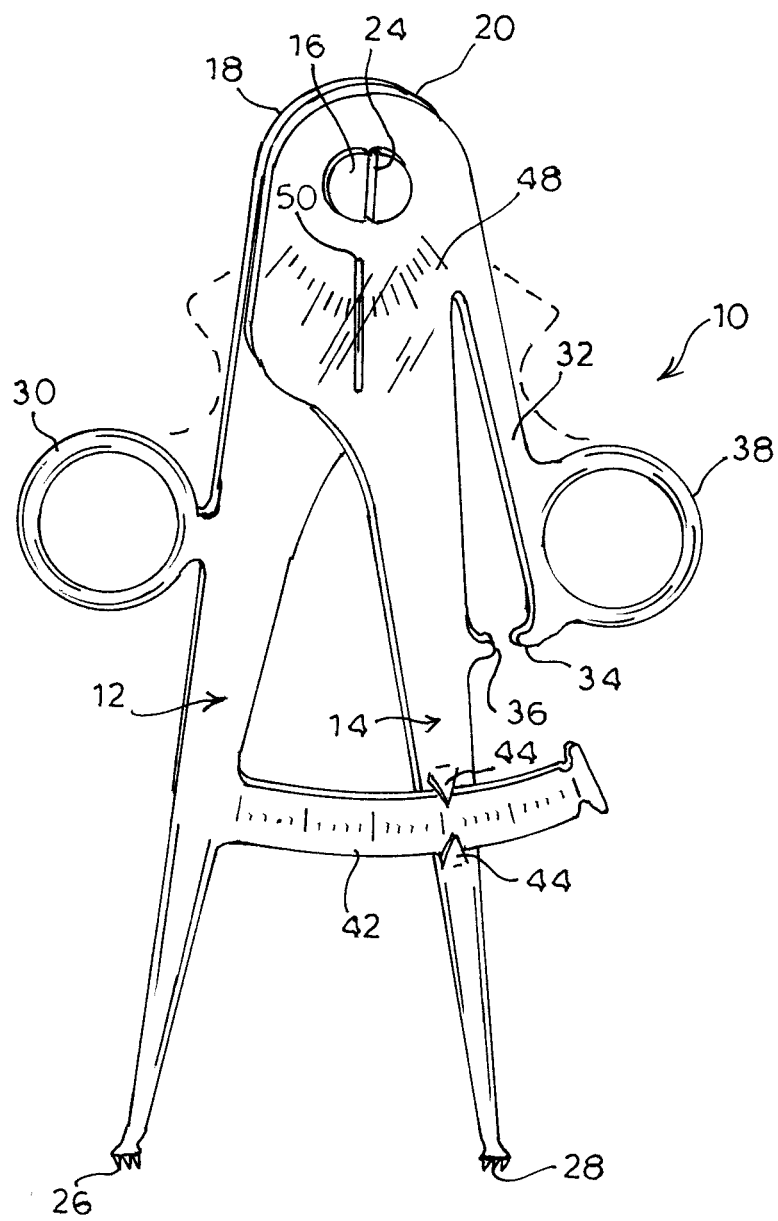
FIG. 1 is a front elevation view of an embodiment of a skin tensiometer.
Figure 2:
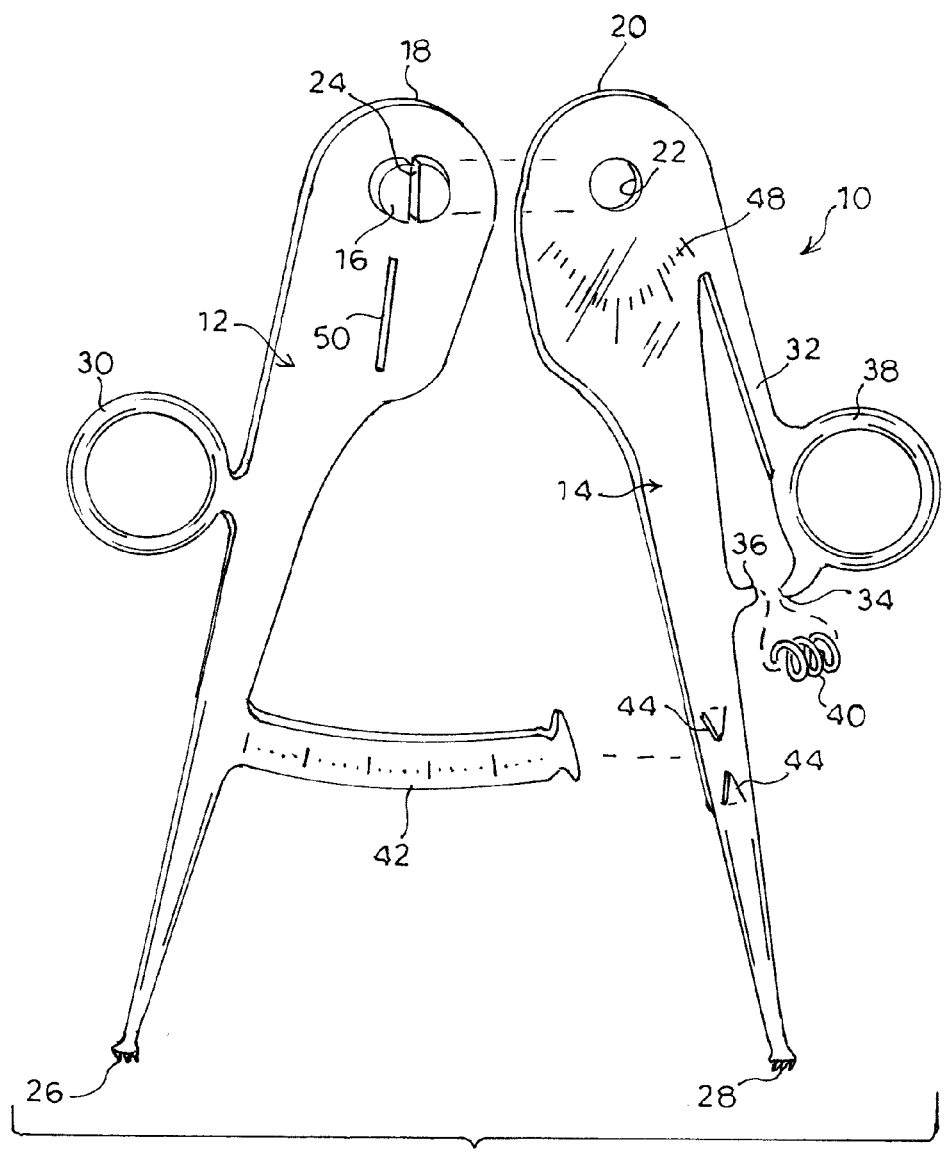
FIG. 2 is an exploded front elevation view of the embodiment of the skin tensiometer as shown in FIG. 1.

Referring now to the drawings, wherein like reference numerals designate corresponding or similar elements throughout the several views, a skin tensiometer is shown in FIGS. 1 and 2 and generally designated at 10. The skin tensiometer 10 comprises a first rigid, elongated leg member 12 and a second rigid, elongated leg member 14. An ear 30 defining a finger opening is integral with the first leg member 12. The first leg member 12 has an ovular tab 16 projecting normally from a proximal end 18. The tab 16 has an outer peripheral flange 17. A proximal end 20 of the second leg member 14 defines an opening 22 for receiving the tab 16 such that the second leg member 14 fits over the first leg member 12. The distal end surfaces 26, 28 of the first and second leg members 12, 14 are serrated for preventing movement relative to the skin when engaging the skin. The distal end surfaces 26, 28 of the first and second leg members 12, 14 may also be cleated, tined or otherwise pointed for engaging the skin to secure the relative position of the distal ends 26, 28 on the skin. Alternatively, the distal ends 26, 28 of the first and second leg members 12, 14 may be formed of various materials including adhesive, or of various textures, as necessary to secure the position of the distal ends 26, 28 on the skin during use.

The tab 16 is adapted to be inserted through the opening 22 in the second leg member 14 such that the flange 17 engages the outer surface of the second leg member 14 that defines the opening 22 for securing the first and second leg members 12, 14 together. For this reason, the tab has a central longitudinal slot 24 rendering the tab 16 resiliently deflectable, which resilience may be easily achieved by proper proportioning of the tab thickness relative to the projecting distance. When connected, the first and second leg members 12, 14 pivot relative to one another at a common point at their proximal ends 18, 20 so that the distal ends 26, 28 of the first and second leg members 12, 14 can be moved between open and closed positions.

An elongated spring arm 32 is affixed adjacent to the second leg member 14 and extends longitudinally toward the distal ends 26, 28 of the first and second leg members 12, 14. A post 34 may extend inwardly from adjacent a distal end of the spring arm 32 and toward the second leg member 14. A stop projection 36 is formed integral with the second leg member 14 and positioned for engagement with the post 34 on the spring arm 32 as the first and second leg members 12, 14 are moved toward one another by relative pivoting of the first and second leg members 12, 14. A second ear 38 defining a finger hole is provided at the distal end of the spring arm 32. Optional curved finger grip surfaces, shown in phantom in FIG. 1, may be formed on the first leg member 12 and the spring arm 32.

In a one-piece construction, a relatively thin integral portion of material interconnects the second leg member 14 and the spring arm 32. In this arrangement, the interconnection inherently resiliently resists engagement of the post 34 and the stop projection 36. As the resilient resistance between the second leg member 14 and the spring arm 32 is overcome by manual force, the post 34 engages the stop projection 36. The stop projection 36 serves as a contact point indicating to the operator while pressing on the spring arm 32 that a predetermined force has been reached. It is understood that the post 34 and the stop projection 36 are not necessary, and contact may simply be between the spring arm 32 and the second leg member 14. Alternatively, or in combination, a spring 40 may be disposed on the post 34 and positioned such that the spring 40 engages the second leg member 14 at one end and the spring arm 32 at the other end. The spring 40 functions to bias the spring arm 32 away from the second leg member 14.

The skin tensiometer 10 may be configured such that a predetermined force exerted on the spring arm 32 is required to move the spring arm 32 into contact with the second leg member 14. Engagement of the post 34 with the stop projection 36 indicates that this level of force applied between the first leg member 12 and the spring arm 32 has been reached. Regardless of the magnitude of the force exerted between the first leg member 12 and the spring arm 32, the necessary force is consistent among uses for repeatable skin tension measurements. It should be appreciated that the material of the skin tensiometer, or the size of the spring 40, can be designed for various clamping forces.

A gauge means 42 is carried by the first leg member 12 for indicating the relative distance between the distal ends 26, 28 of the first and second leg members 12, 14. The gauge 42 extends inwardly from the first leg member 12 and overlaps the second leg member 14. In the embodiment shown, the gauge 42 is integrally formed with the first leg member 12. The gauge 42 is arcuate at approximately the same arc as the arc of the pivoting motion of first and second leg members 12, 14. The surface of the gauge 42 has graduated markings imprinted thereon providing a scale for measuring relative change in position of the leg members. Any desired scale may be used.

The surface of the second leg member 14 has two spaced protrusions 44 defining a slot therebetween for slidingly receiving the gauge 42. The inner ends of the protrusions 44 are preferably beveled as shown. The protrusions 44 function as pointers for convenience in reading the measurements on the gauge 42. Alternatively, the gauge 42 may be readable with reference to either one of the edges of the second leg member 14 to measure the gauged distance between the distal ends 26, 28.

A second gauge 48 may be provided integral with the overlapping proximal ends 18, 20 of the first and second leg members 12, 14. In this embodiment, graduated markings are provided on the surface of the first leg member 12 such as by printing or etching thereon. A reference line 50 is provided on the surface of the second leg member 14. The reference line 50 is visible through the overlapping first leg member 12 such that the reference line 50 may register with the markings on the first leg member.

Figure 3:
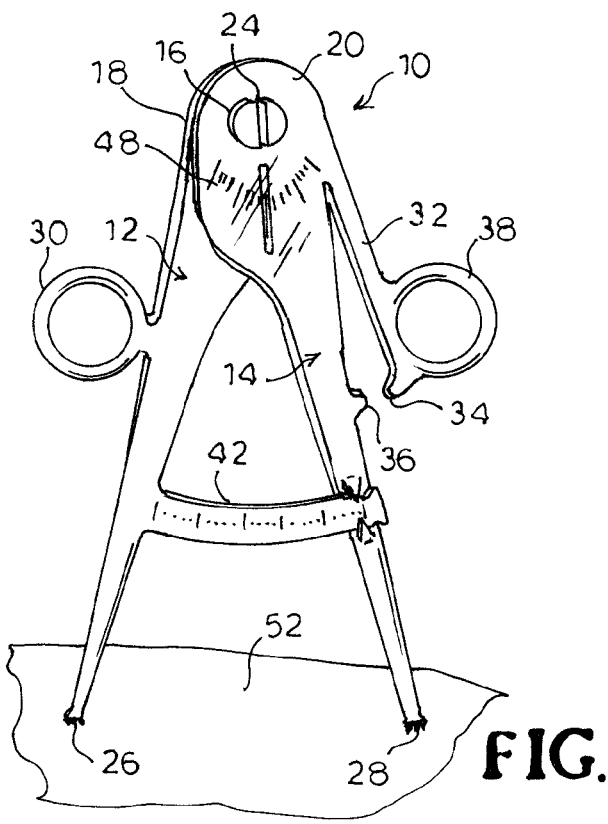
FIG. 3 is a front perspective view of the skin tensiometer as shown in FIG. 1 in a first position engaging a portion of skin at a body site.
Figure 4:
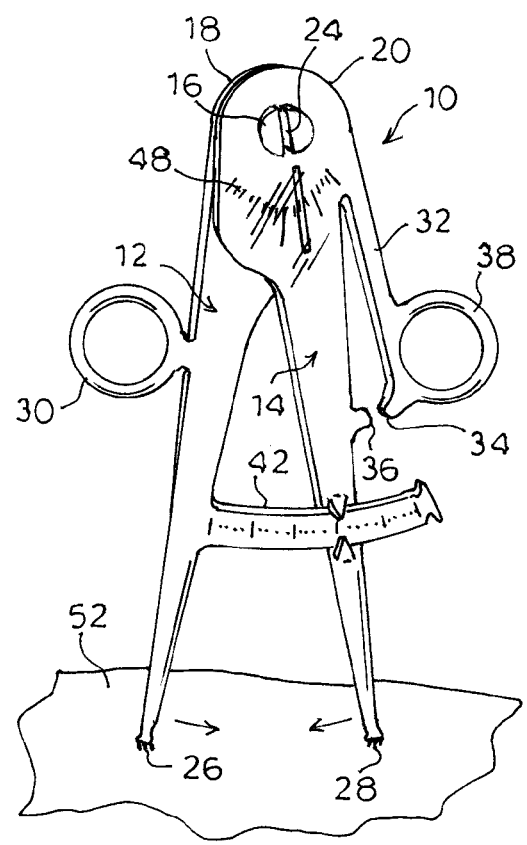
FIG. 4 is a front perspective view of the skin tensiometer engaging the portion of skin as shown in FIG. 3 in a second position.

In use, the operator holds the skin tensiometer 10 in one hand with one finger in each of the finger holes of the ears 30, 38. For example, the thumb and the forefinger can be inserted into the opposite finger holes. The skin tensiometer 10 may be opened such that the pointers 44 on the second leg member 14 register with the zero line on the scale of the gauge 42, although it is not necessary to use the fully open position, especially where space is limited. For example, in all positions of the leg members 12, 14 the pointers or index line is registered with the first gauge 42 or the second gauge 48, respectively. The serrated distal ends 26, 28 of the first and second leg members 12,14 are pressed against a selected portion of the skin 52 in spaced relation as shown in FIG. 3. Inward force is then applied to the finger grips to draw the distal ends 26, 28 of the leg members 12, 14 together to the extent allowed by the skin as the leg members 12, 14 pivot at their proximal pivot point. As the first and second leg members 12, 14 move together, the position of the leg members move relative to the graduated markings on the arcuate gauge 42, the distance of the movement depending on the skin tension. As the operator continues to apply force, the skin tension increases to cause deformation of the spring arm 32 toward the second leg member 14 until the post 34 on the spring arm 32 contacts the stop projection 36 on the second leg member 14, as shown in FIG. 4. This engagement will be discerned by the operator and indicates to the operator that a predetermined force is being applied to the distal ends 26, 28 of the skin tensiometer in the plane of the skin.

When the post 34 engages the stop projection 36, a reading can be made on the scale of either, or both, of the gauge means 42, 48. The reading provides an indication of the relative movement of the leg members 12, 14, and thus the tension of that portion of the skin, by a predetermined, repeatable force. It is understood that the larger relative change in the gauge markings 42, 48 indicates less skin tension. At a higher skin tension, the leg members 12, 14 will not move together as much, so the relative change in the gauge markings 42, 48 will be less before the post 34 engages the stop projection 36. As soon as this reading has been accomplished, the force being applied to the finger grips can be released, or the device 10 can be lifted away from the skin in order to disengage the serrated distal 26, 28 ends of the first and second leg members 12, 14 from the skin surface.

Other embodiments of the skin tensiometer may include other means for indicating that the predetermined force or pressure level is reached. For example, an audible sound may be emitted signaling the operator as an indication of the pressure level. An electronic sensor may also be used to monitor the strain on the spring arm and to signal the operator. The sensor emits an audible or visual signal when the predetermined pressure level is reached so the operator knows that the appropriate pressure has been achieved.

Although a skin tensiometer has been shown and described in considerable detail with respect to only a few exemplary embodiments thereof, it should be understood by those skilled in the art that I do not intend to limit the description to the embodiments since various modifications, omissions and additions may be made to the disclosed embodiments without materially departing from the novel teachings and advantages of the skin tensiometer, particularly in light of the foregoing teachings. For example, the components can be made separately and joined by fasteners or other means. In addition, skin tension can be measured by spreading the leg members since skin tension is determined by relative movement of the leg members after engaging the skin. Accordingly, I intend to cover all such modifications, omission, additions and equivalents as may be included within the spirit and scope of the description as defined by the following claims. In the claims, means-plus-function clauses are intended to cover the structures described herein as performing the recited function and not only structural equivalents but also equivalent structures.

Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

I claim:

1. An apparatus for measuring tension of skin, the skin tension measuring apparatus comprising:
   a first rigid leg having a longitudinal axis, the distal end of the first leg terminating in a surface generally transverse to the longitudinal axis of the first leg;
   a second rigid leg having a longitudinal axis, the distal end of the second leg terminating in a surface generally transverse to the longitudinal axis of the second leg;
   means for pivotally connecting proximal ends of the first leg and the second leg such that distal ends of the first leg and the second leg can be moved toward and away from one another;
   a gauge carried by one of the first leg or the second leg for giving an indication of the spacing between the distal ends of the first leg and the second leg;
   indicia carried by the other of the first leg or the second leg; and
   a spring arm connected for resilient, flexible movement relative to one of the first leg or the second leg,
   wherein the distal end surface of the first leg and the distal end surface of the second leg are adapted to engage the skin such that tension may be applied to the skin by movement of the first leg or the second leg relative to the other.

2. The skin tension measuring apparatus of claim 1, wherein the spring arm is formed integral with one of the first leg or the second leg for requiring a predetermined force between the other first leg or the second leg to move the spring arm and the one of the first leg or the second leg towards a closed position.

3. The skin tension measuring apparatus of claim 2 wherein the spring arm is positioned so that it can be engaged by one finger of a hand while another finger of the same hand can be utilized to engage the other leg to apply the predetermined force between the ends of the first leg and the second leg.

4. The skin tension measuring apparatus as in claim 2 wherein the gauge means carried by the one leg comprises means for determining when the predetermined clamping force is being applied between the distal ends of the first leg and the second leg.

5. The skin tension measuring apparatus as in claim 1 together with means carried by the first and second legs for yieldably urging the first and second arms towards the open position.

6. The skin tension measuring apparatus as in claim 1 together with stop means carried by the one arm for preventing deflection of the spring arm beyond a predetermined amount.

7. The skin tension measuring apparatus as in claim 1 wherein the cooperative gauge means carried by the one of the first arm and the second arm for indicating the spacing between the ends of the first and second arms includes an arcuate member carried by one of the arms, the other of the arms having a slot formed therein and adapted to receive the arcuate gauge member and means carried by the other of the arms and the arcuate gauge member for limiting movement of the other arm with respect to the gauge member.

8. The skin tension measuring apparatus as in claim 7 wherein the gauge member is provided with a distal stop extending transversely thereof and a pointer carried by the other arm engaging the stop.

* * * * *